US00PP13693P29

(12) United States Plant Patent
Sato

(10) Patent No.: US PP13,693 P2
(45) Date of Patent: Apr. 1, 2003

(54) *LOROPETALUM CHINENSE* VARIETY *RUBRUM* NAMED 'MOSAIC'

(75) Inventor: Noboru Sato, Angyo Kichi Zo (JP)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 10/074,776

(22) Filed: Feb. 11, 2002

(51) Int. Cl.[7] ..... A01H 5/00
(52) U.S. Cl. ..... Plt./226
(58) Field of Search ..... Plt./226

*Primary Examiner*—Bruce R. Campell
*Assistant Examiner*—W C Haas
(74) *Attorney, Agent, or Firm*—Christie, Parker & Hale, LLP

(57) ABSTRACT

A new plant variety of *Loropetalum chinense* variety *rubrum* characterized by its sectoral Yellow variegation.

1 Drawing Sheet

BACKGROUND OF THE INVENTION

Figure 1:
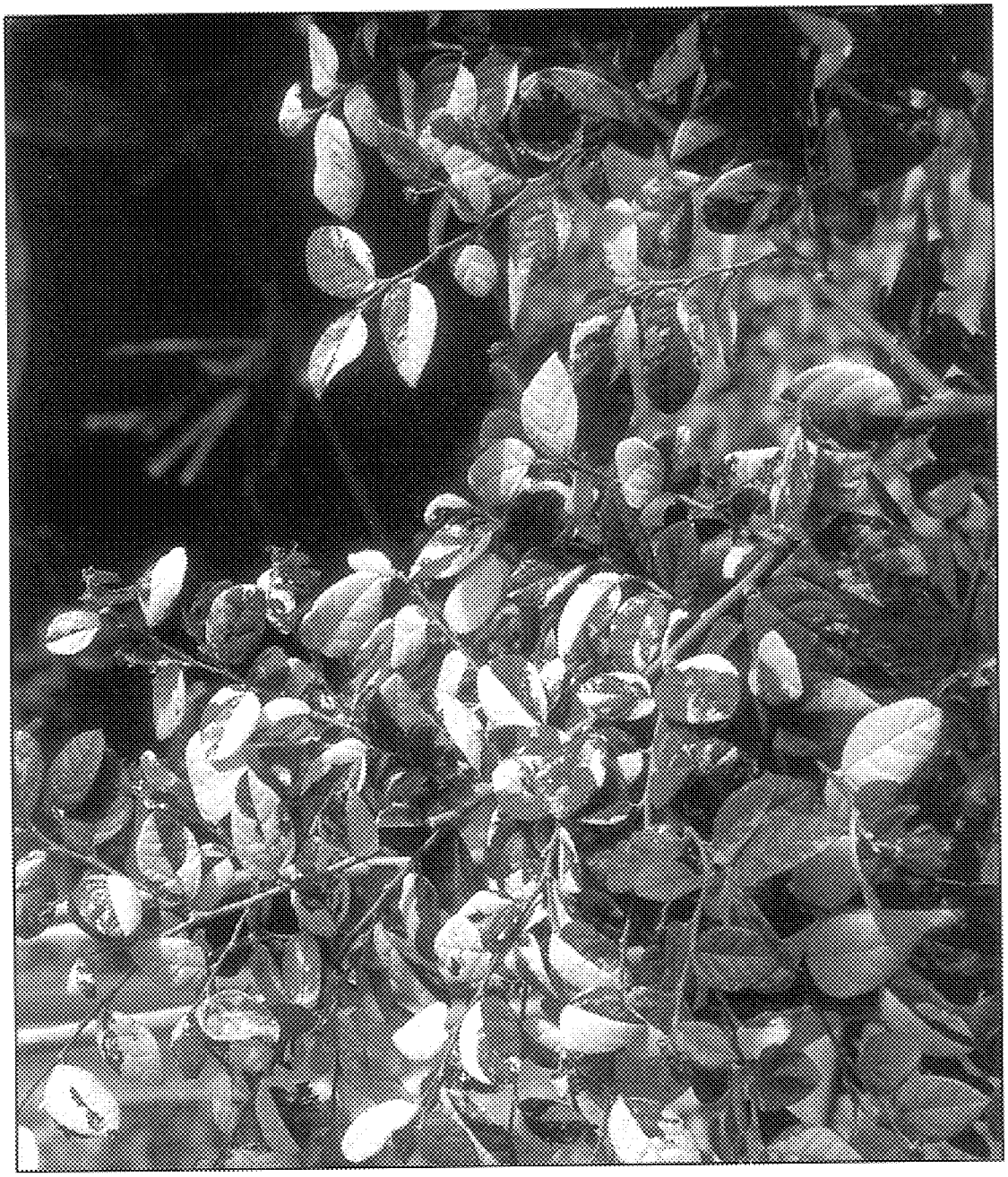

The present invention relates to a new and distinct variety of *Loropetalum chinense* variety *rubrum* Yieh and was discovered as a branch sport of an unnamed variety of *Loropetalum chinense* var. *rubrum* (unpatented) in Saitama Prefecture, Japan. The varietal denomination of the new variety is 'MOSAIC'.

The genus Loropetalum is included in the family Hamamelidaceae that comprises about 15 genera of shrubs and trees growing in the northern hemisphere. Loropetalum comprises one (1) species of evergreen shrub or small tree, which possesses desirable ornamental characteristics. Loropetalum was first introduced to Europe as an ornamental plant the 1880s, and is believed to have been cultivated in North America since the early 1930s.

*Loropetalum chinense* var. *rubrum* is a native of China, and was first discovered in 1928 in Hunan Province. It was rediscovered in the late 1980s and subsequently introduced to the United States. *Loropetalum chinense* var. *rubrum* generally has alternate, ovate leaves to about 6 cm long and about 3 cm wide. The plant is evergreen or partly evergreen depending on winter temperature. Leaf color ranges from light to dark Burgundy, occasionally Green, depending on light intensity, cultural conditions and cultivar. Shoots are slender, Brown, and densely pubescent, pith is solid. Leaves are generally densely pubescent overall.

Flowers of *Loropetalum chinense* var. *rubrum* are perfect, having 4-strap like petals which are about 2 cm long and about 0.3 cm wide. Three (3) to six (6) flowers are together in each leaf axil. Pedicel and calyx have a White pubescence. Flower color is Pinkish to Reddish Purple depending on the cultivar. Flowering is heaviest in early spring.

SUMMARY OF THE INVENTION

The new variety was discovered as a branch sport, and differs from other cultivars known to the inventor by its sectoral Yellow leaf variegation. Asexual reproduction of the new variety by stem cuttings performed in Kawaguchi City, Saitama Prefecture, Japan; and Fulshear, Tex. have confirmed that the distinctive characteristics of the new variety are stable and transmitted to succeeding generations and that the new variety reproduces true to type.

COMPARISON WITH PARENT

'MOSAIC' is distinguished from its parent and all other varieties of *Loropetalum chinense* var. *rubrum* of which I am aware by its sectoral Yellow variegation. In contrast, the parent of 'MOSAIC' exhibits solid Purple foliage. Named varieties similar to the parent include *Loropetalum chinense* var. *rubrum* 'Ruby' (unpatented), and 'Hines Purpleleaf' (unpatented), both of which exhibit solid Purple foliage.

BRIEF DESCRIPTION OF ILLUSTRATION

The accompanying photographic illustration shows a plant of the new cultivar as true to color as is reasonably possible to make in an illustration of this character.

FIG. 1 illustrates the distinctive sectoral Yellow leaf variegation.

DESCRIPTION OF THE NEW VARIETY

*Loropetalum chinense* var. *ruburm* 'MOSAIC' has not been observed under all possible environmental, cultural and light conditions. The following observations and descriptions are of two-year-old plants grown in 5-gallon nursery containers in Fulshear, Tex. Phenotypic expression may vary with light intensity, cultural, and environmental conditions. In this description, color references are to The Royal Horticultural Society Colour Chart (1995) and terminology used in the color descriptions herein refers to plate numbers in this color chart.

As with many plants in the Hamamelidaceae family, phenotypic characteristics can be dramatically different in terms of growth morphology.

Botanical classification: *Loropetalum chinense* var. *rubrum* 'MOSAIC'.

*Parentage.*—Branch sport of an unnamed variety of *Loropetalum chinense* var. *rubrum* (unpatented).

*Propagation.*—Vegetative cuttings.

Plant:

*Size.*—To about 5 feet tall and about 6 to 8 feet wide.

*Habit.*—Young plants exhibit pendulous growth habit. Once plant is established, plant exhibits upright growth habit on growth.

Branching: Dense, overall mounding to upright branching habit.

*Lateral branches.*—Multi-branched shrub. Typical Branch Quantity: More than 1,000 branches and stems.

*Observed branch quantity.*—More than 1,000 branches and stems.

*Size.*—Typical branch is about 1 m long, pendulous; diameter about 1 cm; apex is typically 1 mm or less.

*Branch coloration.*—Near Grayed-Orange Group 166A.

Leaf:

*Shape.*—Ovate to obovate.

*Size.*—Young foliage: Length about 1.4 cm; width about 1 cm wide. Mature foliage: Length about 3.4 cm; width about 2.2 cm.

*Arrangement.*—Simple, alternate along the stem.

*Margin.*—Entire, with stellate hairs.

*Texture.*—Adaxial: coriaceous; sparsely pubescent with stellate hairs.

*Apex.*—Acute to obtuse.

*Base.*—Obtuse, occasionally unequal.

Color: Color varies with intensity of sunlight and cultural conditions. The following color readings were taken on Sep. 28, 2001 in full sun of a specimen grown in Fulshear, Tex. Sectoral Yellow variegations emerges as foliage reaches maturity. The amount and precise pattern of variegation varies from leaf to leaf, but generally covers about 50% of the leaflets.

*New foliage.*—Adaxial: Near Greyed-Purple Group 187A. Abaxial: Near Greyed-Purple Group 183C.

*Mature foliage.*—Adaxial: Background color mostly near Yellow-Green Group 147A with some areas near Yellow-Green Group 145C and 148B; variegated areas vary from near Yellow Group 4C with some areas near Yellow Group 7B and 9C. Abaxial: Background color near Yellow-Green Group 148C; variegated areas near Yellow Group 4C and 10C.

*Venation pattern.*—Pinnate.

*Petioles.*—Size: Length between 2 to 4 mm; diameter about 1 mm. Color Young foliage: Near Greyed-Red Group 182B. Mature foliage: Near Green Group 139B.

*Stipules.*—Between 2 to 3 mm; color near Yellow-Green Group 146C.

*Internodes.*—Between 0.5 to 2 cm.

*Hardiness.*—USDA Zone 7 (0° F. to 7° F.).

*Vigor.*—Moderate.

*Pests/diseases.*—None noted.

Inflorescence:

*Bloom period.*—Between March to April in Fulshear, Tex. with light repeat blooming throughout the growing season.

*Flowering habit.*—Globose heads on terminals; occasionally solitary in the leaf axils.

*Quantity.*—Between 5 to 7 flowers in a globose head.

*Form.*—Perfect, with 4 strap-like petals; forming a loose funnel; petal count can be as high as 6.

*Size.*—Diameter about 2.3 cm; height about 2.2 cm.

*Fragrance.*—None noted.

Longevity on plant: About 4 to 5 days.

Petalage:

*Color.*—Adaxial: Near Red-Purple 61A. Abaxial: Near Red-Purple 61A.

*Arrangement.*—4 arising from calyx tube at sepal base; some flowers may have up to 6.

*Shape.*—Linear.

*Margin.*—Entire.

*Apex.*—Retuse.

*Size.*—About 17 cm long and 3 mm wide.

*Texture.*—Smooth.

*Buds.*—Shape: Orbicular. Size: Length about 3 mm; diameter about 3 mm. Color: Near Red-Purple Group 59D. Rate of opening: About 5 to 7 days.

*Penduncle.*—Size: Length about 3 mm; diameter about 1 mm. Color: Near Red-Purple Group 59C. Aspect: Horizontal to slightly erect in stem axils. Texture: Pubescent.

*Sepals.*—Attangement: Opposite; about 4 per flower; calyx erect and cruciform. Shape: Ovate with a pointed apex and an entire margin. Size: Length about 3 mm; width about 2 cm. Color: Outer surface near Red-Purple Group 58A; inner surface near Red-Purple Group 61A. Texture: Pubescent.

Reproductive organs:

*Stamens.*—About 4.

*Pistils.*—About 2.

*Pollen.*—Typical Amount Produced: Minute. Observed Amount Produced: None observed.

*Fruit.*—Loculicidal capsule. Quantity: Between 75 to 100 per plant per year. Size: Length about 5 mm; diameter about 6 mm. Color: Near Grey-Brown Group 199A.

I claim:

1. A new plant variety of *Loropetalum chinense* variety *rubrum* of the variety substantially as shown and described.

* * * * *